United States Patent [19]

Haag et al.

[11] 4,374,296
[45] Feb. 15, 1983

[54] ISOMERIZATION OF PARAFFIN HYDROCARBONS USING ZEOLITES WITH HIGH STEAM-ENHANCED ACIDITY

[75] Inventors: Werner O. Haag, Lawrenceville, N.J.; Rudolph M. Lago, Yardley, Pa.

[73] Assignee: Mobil Oil Corporation, New York, N.Y.

[21] Appl. No.: 249,564

[22] Filed: Mar. 31, 1981

Related U.S. Application Data

[63] Continuation-in-part of Ser. No. 121,339, Feb. 14, 1980, Pat. No. 4,326,994.

[51] Int. Cl.$^3$ .............................................. C07C 5/13
[52] U.S. Cl. ........................... 585/739; 208/138; 252/455 Z; 252/459; 585/481
[58] Field of Search ............. 585/739, 751, 481; 252/179, 455 Z, 459; 208/138

[56] References Cited

U.S. PATENT DOCUMENTS

| | | | |
|---|---|---|---|
| 3,301,917 | 1/1967 | Wise | 252/455 Z |
| 3,308,069 | 5/1967 | Wadlinger et al. | 252/455 |
| 3,370,099 | 2/1968 | Plank et al. | 252/455 Z |
| 3,432,568 | 3/1969 | Miale et al. | 252/455 Z |
| 3,493,490 | 2/1979 | Plank et al. | 208/120 |
| 3,541,027 | 11/1970 | Lapides | 252/455 |
| 3,672,267 | 6/1972 | Chen et al. | 252/455 Z |
| 3,700,585 | 10/1972 | Chen et al. | 208/111 |
| 3,702,886 | 11/1972 | Arganer et al. | 252/455 Z |
| 3,758,403 | 9/1973 | Rosinski et al. | 208/120 |
| 3,766,056 | 10/1973 | Young et al. | 208/111 |
| 4,016,218 | 4/1977 | Haag et al. | 260/671 |
| 4,021,447 | 5/1977 | Rubin et al. | 260/326.8 |
| 4,083,889 | 4/1978 | Caesar et al. | 260/682 |
| 4,324,696 | 4/1982 | Miale | 252/455 Z |

FOREIGN PATENT DOCUMENTS

| | | | |
|---|---|---|---|
| 882681 | 10/1971 | Canada | 252/60 |
| 2089354 | 1/1972 | France | 33/00 |
| 2312478 | 12/1976 | France | 3/52 |
| 2348153 | 11/1977 | France | 33/28 |
| 1394979 | 5/1975 | United Kingdom | 3/00 |

Primary Examiner—Delbert E. Gantz
Assistant Examiner—A. Pal
Attorney, Agent, or Firm—Charles A. Huggett; Michael G. Gilman; Stanislaus Aksman

[57] ABSTRACT

A process is provided for effecting hydroisomerization of a $C_4$–$C_8$ paraffin by contacting the same under hydroisomerization conditions with a catalyst comprising a porous crystalline zeolite characterized by a silica/aluminum mole ratio of greater than 12 and a constraint index within the approximate range of 1 to 12, which zeolite has undergone controlled pretreatment by contact with water to enhance the acid activity thereof, expressed as alpha, to greater than about 300. The catalyst also comprises, intimately combined therewith, a minor proportion of a Group VIII metal.

23 Claims, 1 Drawing Figure

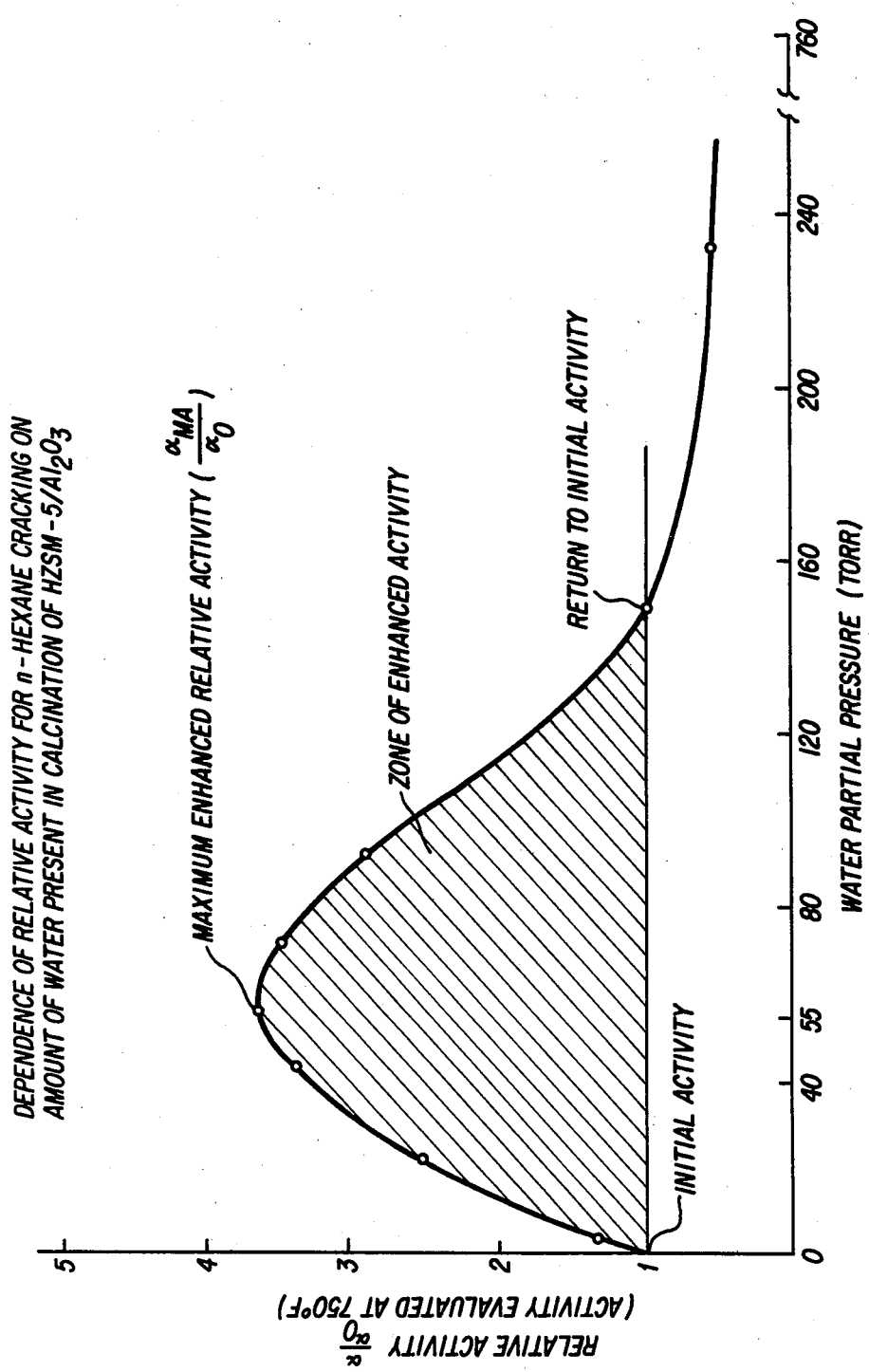

ISOMERIZATION OF PARAFFIN HYDROCARBONS USING ZEOLITES WITH HIGH STEAM-ENHANCED ACIDITY

CROSS REFERENCE TO RELATED APPLICATIONS

This application is a continuation-in-part of a copending application Ser. No. 121,339, filed Feb. 14, 1980, now U.S. Pat. No. 4,326,994, dated Apr. 27, 1982.

BACKGROUND OF THE INVENTION

1. Field of the Invention

This invention relates to a process for effecting isomerization of paraffins, including normal paraffins and/or cycloparaffins, in the presence of hydrogen and a catalyst comprising a highly siliceous porous zeolite crystalline material of controlled enhanced acid activity characterized by a silica/alumina mole ratio of greater than about 12 and a constraint index, hereinafter defined, within the approximate range of 1 to 12, which zeolite has intimately combined therewith a minor proportion of a Group VIII metal.

2. Description of the Prior Art

It has heretofore been known that the isomerization of paraffins, such as n-hexane, to equilibrium mixtures of branched chain isomers, substantially increases the octane rating of the paraffin hydrocarbons. Prior art processes dealing with paraffin isomerization include a liquid-phase process utilizing a catalyst containing an aluminum chloride dissolved in antimony trichloride, which, together with HCl formed during the reaction, are corrosive. Another process, referred to as the Penex process, which has been used for isomerizing pentane and hexane fractions from refinery naphthas and natural gasolines in the presence of hydrogen and a platinum containing catalyst requires the continuous addition to the feed of an organic chloride which also produces HCl. Another process involves reaction of a pentane/hexane feed in the presence of hydrogen and a catalyst containing platinum highly dispersed on hydrogen mordenite at a pressure of 150–350 psi and a temperature of 400 to 550 degrees F. with a maximum water level in the feed of 50 ppm. The above processes have been costly to operate because of extensive corrosive effects attributable to the use of highly acidic catalysts or by-products arising from use of such catalyst, thereby requiring expensive alloy equipment. Moreover, moisture and high molecular weigtt hydrocarbons usually present as contaminants in the charge stock cause deterioration of the catalyst and necessitate frequent replacement thereof. Another process which has been carried out at a higher temperature of 700 to 800 degrees F. utilizes a catalyst such as platinum on a silica-alumina base in the presence of hydrogen. At the high temperatures required, the equilibrium mixture of isomers is such that substantial recycling of a portion of the paraffin feed is necessary to obtain the desired improvement in octane rating.

Prior patents dealing with paraffin isomerization include U.S. Pat. No. 3,432,568 which describes hydroisomerization of saturated aliphatic and cyclic hydrocarbons by contacting with a mixed dual-functional catalyst comprising hydrogen mordenite and a dehydrogenation component supported on a thermally stable carrier. U.S. Pat. No. 3,301,917 relates to hydroisomerization of paraffinic hydrocarbons in the presence of a mixed catalyst consisting essentially of an acid aluminosilicate portion and a hydrogenation component of a platinum metal supported on a thermally stable carrier. U.S. Pat. No. 3,673,267 describes process for isomerization of paraffinic hydrocarbons under isomerizing conditions and in the presence of hydrogen with a catalyst of hydrogen mordenite having a silica to alumina mole ratio between about 20:1 and about 60:1, having associated therewith a metal of Group VIII, Group VIB or Group IB. U.S. Pat. No. 3,370,099 is concerned with hydroisomerization of isomerizable hydrocarbons in the presence of a catalyst composition of an aluminosilicate containing at least 0.5 equivalents per gram atom of aluminum of metal cations of which at least some and generally 50 percent or more of the total equivalents are cations of a rare earth metal. U.S. Pat. No. 3,702,886 describes crystalline zeolite ZSM-5 and indicates that the same may be used as a catalyst for hydroisomerization of normal paraffins when provided with a hydrogenation component, such as platinum.

SUMMARY OF THE INVENTION

The present invention contemplates the upgrading of normal paraffinic hydrocarbons or cycloparaffins by hydroisomerization in the presence of a specified highly siliceous porous zeolite crystalline material of enhanced acid activity having a minor proportion of a Group VIII metal combined therewith. In addition, the invention described herein involves continuous hydroisomerization of normal paraffins or cycloparaffins for extended periods of time in the presence of hydrogen and the above indicated catalyst so as to produce a mixture of branched chain isomers having a high octane rating without the use of corrosion resistant alloy equipment or frequent replacement of catalyst material. In addition, this invention is directed to the hydroisomerization of n-pentane, n-hexane or mixtures thereof in the presence of hydrogen and a specified catalyst comprising a porous crystalline zeolite of enhanced acid activity and defined silica/alumina mole ratio and constraint index and having a minor proportion of platinum, supported on an alumina carrier under specified reaction conditions.

In accordance with the present invention, it has been found that marked improvements are realized in a process for isomerizing paraffinic hydrocarbons admixed with hydrogen in the presence of a catalyst comprising a highly siliceous porous zeolite crystalline material having an acid activity, expressed as an alpha value, of at least about 300, generally in the approximate range of 300 to 10,000 and preferably between about 300 and about 5,000. The highly siliceous porous zeolite crystalline material employed is further characterized by a silica/alumina mole ratio of greater than about 12 and a constraint index, hereinafter defined, within the approximate range of 1 to 12, which zeolite has intimately combined therewith a minor proportion, generally in the range of 0.01 to 10 weight percent, of a Group VIII metal, which is preferably platinum or palladium.

Isomerization of both, cycloparaffins such as cyclohexane to methyl cyclopentane, and isomerization of light paraffinic hydrocarbons of $C_4$, $C_5$ and $C_6$ paraffins and mixtures thereof has been effectively carried out with improved conversion and high selectivity to an iso-paraffin product.

Isomerization, in accordance with the present process, is carried out at a temperature between about 200 and about 900 degrees F., preferably between about 300 and about 750 degrees F., with a liquid hourly space velocity between about 0.1 and about 50, preferably about 0.2 and about 10 at a pressure between 0 and about 1,000 psig in the presence of an amount of hydrogen such that the hydrogen to hydrocarbon mole ratio is between about 0.1:1 and about 20:1.

Enhancement in the acid activity of the above described process zeolite is achieved by treatment with water, i.e., liquid water or steam under controlled conditions, as more particularly set forth in our copending application Ser. No. 121,339, filed Feb. 14, 1980, the entire contents of which are incorporated herein by reference.

The conditions effecting enhancement of the porous zeolite depend on the interrelationship of several variables such as temperature, water partial pressure, treating time, nature of the zeolite and nature of treating gas. There exists a "zone of enhanced activity" where acid activity is increased over initial activity. Under conditions that are too mild, catalyst activation is not obtained. Alternatively, under too severe conditions, the catalyst will undergo deactivation. Under conditions of constant temperature, the following expression approximately describes the relationships of the two variables, treating time and water partial pressure:

$$0.01(Pt)_T < (Pt) < 10(Pt)_T$$

where
$(Pt)_T = 2.6 \times 10^{-9} e^{16000/T}$;
P = Water Partial Pressure, atmospheres;
t = Treating Time, hours;
T = Temperature, degrees K.

It has further been established that under the above controlled water treating conditions, ammonia addition to the water yields even higher activities than the treatment with water alone.

The resulting hydrocarbon isomers produced by the process of the invention are useful as gasoline blending stocks because of their high anti-knock properties. In addition, isomerization of n-butane to isobutane provides the latter for olefin alkylation units, another source of high octane gasoline.

BRIEF DESCRIPTION OF THE DRAWING

The drawing is a plot of relative activity for n-hexane cracking versus water partial pressure in the calcination of HZSM-5/Al$_2$O$_3$.

DESCRIPTION OF SPECIFIC EMBODIMENTS

Following the teachings of the present invention, a hydrocarbon feed stock containing C$_4$ to C$_8$ paraffins, e.g., C$_4$–C$_6$ normal paraffins, or cycloparaffins, such as cyclohexane, is contacted under hydroisomerization conditions with a catalyst comprising a porous zeolite characterized by a silica/alumina ratio of greater than about 12 and a constraint index within the approximate range of 1 to 12, which zeolite has undergone a controlled pretreatment to enhance the acid activity thereof, so that its acid activity, expressed as alpha value is greater than about 300, and which contains a Group VIII metal incorporated therein.

Feedstocks employed in the present process include straight run C$_4$, C$_5$, C$_6$ or C$_5$–C$_6$ fractions, C$_5$–C$_7$ raffinate cuts from solvent extraction units which are processing catalytic reformates or pyrolysis gasoline from ethylene crackers. Paraffinic hydrocarbon feedstocks useful in the present process may be a substantially pure normal paraffin having from four to eight carbon atoms, mixtures of such substantially pure paraffins or a cycloparaffin-containing charge, i.e., cyclohexane.

The porous zeolite used herein comprises a crystalline zeolite which is a member of a class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina mole ratios, they are very active even when the silica to alumina mole ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of silicon atoms interconnected by oxygen. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intercrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type of zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of the 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000 degrees F. for at least 15 minutes. The zeolite is then flushed with helium and the temperature adjusted between 550 degrees F. and 950 degrees F. to give an overall conversion between 10 percent and 60 percent. The mixture of hydrocarbons is passed at a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550 degrees F. to 950 degrees F., with accompanying conversion between 10 percent and 60 percent, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60 percent for most catalyst samples and represents preferred conditions, it may occasionally be necessary to use somewhat more severe conditions for samples of very low activity, such as those having a very high silica to alumina mole ratio. In those instances, a temperature of up to about 1000 degrees F. and a liquid hourly space velocity of less than one, such as 0.1 or less, can be employed in order to achieve a minimum total conversion of about 10 percent.

The class of zeolites defined herein is exemplified by ZSM-5, ZSM-11, ZSM-12, ZSM-23, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000 degrees F. for one hour, for example, followed by base exchange with ammonium salts followed by calcination at 1000 degrees F. in air. The presence of organic cations in the forming solution may not be absolutely essential to the formation of this type zeolite; however, the presence of these cations does appear to favor the formation of this special type of catalyst by base exchange with ammonium salts followed by calcination in air at about 1000 degrees F. for from about 15 minutes to about 24 hours.

Natural zeolites may sometimes be converted to this type of zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are ZSM-5, ZSM-11, ZSM-12, ZSM-23, ZSM-35 and ZSM-38, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5-11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the original alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

In practicing the desired method, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The degree of zeolite catalyst activity for all acid catalyzed reactions can be measured and compared by means of "alpha value" ($\alpha$). The alpha value reflects the relative activity of the catalyst with respect to a high activity silica-alumina cracking catalyst. To determine the alpha value as such term is used herein, n-hexane conversion is determined at a suitable temperature between about 500 degrees F. to 1000 degrees F., preferably at 1000 degrees F. Conversion is varied by variation in space velocity such that a conversion level of up to about 60 percent of n-hexane is obtained and converted to a rate constant per unit volume of zeolite and compared with that of silica-alumina catalyst which is normalized to a reference activity of 1000 degrees F. Catalytic activity of the catalysts is expressed as multiple of this standard, i.e., the silica-alumina standard. The silica-alumina reference catalyst contains about 10 weight percent $Al_2O_3$ and the remainder $SiO_2$. This method of determining alpha, modified as described above, is more fully described in the "Journal of Catalysis", Vol. VI, pages 278–287, 1966, the entire contents of which are incorporated herein by reference.

One measure of comparison used to relate catalyst activities is "relative activity." Relative activity is the ratio of the activity of the catalyst after treatment over the initial activity. Thus, relative activity can be expressed as follows:

$$\text{Relative Activity} = \frac{\alpha}{\alpha^\circ}$$

The relative activity of a catalyst at the point of initial activity is therefore one since:

$$\frac{\alpha}{\alpha^\circ} = \frac{\alpha^\circ}{\alpha^\circ} = 1.$$

The relative activity of a catalyst at the point of maximum enhanced activity can be expressed as follows:

$$\text{Relative Activity} = \frac{\alpha}{\alpha^\circ} = \frac{\alpha MA}{\alpha^\circ}.$$

In order to increase the activity of members of this unique class of zeolites, said zeolites are treated with water, in liquid or gaseous form, e.g., steam, or water, or steam, produced in-situ. Non-limiting examples of steam produced in-situ include alcohol dehydration to produce olefins and steam; and hydrocarbon or coke combustion in the presence of oxygen to form carbon oxides and steam.

During treatment, the zeolite should be at least partially in the acidic form, e.g., hydrogen form. Suitable zeolitic forms also include those that are at least partially convertible to the hydrogen form under treatment conditions, e.g., the ammonium form, or alkyl ammonium form.

There exists a narrow range or band of conditions in which zeolite catalyst activity can be enhanced over the initial activity value. Deviations from this band of conditions can result in either non-enhancement of activity (too mild conditions), or alternatively, catalyst deactivation (too severe conditions). Such conditions include temperature, water partial pressure, treating time, nature of the zeolite, and the nature of the treating gas.

This range of conditions can be clearly demonstrated by a plot of relative activity versus a particular variable, e.g., water partial pressure, treating time, etc., with the other conditions being held constant. Such a plot is given by the drawings in which relative activity is plotted against water partial pressure with temperature and treating time being held constant. With increasing water partial pressure, activity is continuously enhanced above initial relative activity until a point of maximum enhanced relative activity is attained ($\alpha MA/\alpha°$). Once maximum enhanced relative activity is achieved, the activity begins to decrease with increasing water partial pressure, ultimately back to the same activity as the initial relative activity (same activity as the untreated zeolite, i.e., initial activity). Increasing water partial pressure after this return to initial activity will eventually result in catalyst deactivation (too severe conditions).

Catalyst activation occurs in a limited region of conditions which can be defined as a "zone of enhanced activity." This zone encompasses those conditions which yield activities greater than the initial activity ($\alpha°$). Thus, the zone is that area bounded by the activity of an untreated catalyst-initial activity and the activity of the catalyst when it returns to the initial activity. In terms of relative activities, the zone of enhanced activity is that area bounded by the initial relative activity ($\alpha°/\alpha° = 1$) and the return to initial relative activity ($\alpha/\alpha° = 1$). The zone of enhanced activity embraces all conditions and combinations thereof yielding activities greater than the initial catalyst activity. One such activity in this zone is the maximum activity. An expression to approximately define this band in relation to two specific variables treating time and water partial pressure, with temperature held constant is as follows:

$$0.01(Pt)_T < (Pt) < 10(Pt)_T$$

where
$(Pt)_T = 2.6 \times 10^{-9} e^{16000/T}$;
P = Water Partial Pressure, atmospheres;
t = Treating Time, hours;
T = Temperature, degrees K.

In regard to the condition of zeolite nature, two particular factors can be evaluated. One factor is the specific zeolite employed, such as ZSM-5, ZSM-11, ZSM-12, ZSM-23, ZSM-35, ZSM-38, etc. Another factor is the crystal size of the particular zeolite employed. For the purposes of this disclosure, small crystal size zeolites are those generally of 0.02 to 0.05 microns and large crystal size zeolites are those of generally 0.1 microns and greater.

The use of large crystal size zeolites rather than small crystal size zeolites has the effect of extending the zone of enhanced catalytic activity. Whereas both large and small size zeolites would conform to the above given relationship of $0.01(Pt)_T < (Pt) < 10(Pt)_T$, for only small size zeolites, the following preferred range is also applicable:

$$0.01(Pt)_T < (Pt) < 1.0(Pt)_T.$$

The extent of the zone of enhanced activity can also be modified by adjustments in the controlled conditions of treating time, temperature and water partial pressure. The interdependence of these variables (controlled conditions) are such that, for example, an increase in water partial pressure, at constant temperature, will lessen the required treating time to attain a certain activity enhancement. Likewise, increasing the temperature, at constant water partial pressure also lessens the required treating time to attain a specific activity enhancement.

The nature of the treating gas is another influential factor in catalyst activity enhancement. The treating gas in all cases contains either steam or steam producing compounds and mixtures. However, when ammonia is a constituent of the treating gas, even greater zeolite maximum activities than those attainable by steam alone can be achieved. Also the zone of enhanced activity is extended. The preferred range for ammonia addition is from about 0.01 to about 10 mole ratio ammonia/steam and more preferably from about 0.1 to about 1.0 mole ratio ammonia/steam.

The catalyst of this invention comprises a porous zeolite of enhanced acid activity containing a minor proportion of a Group VIII metal. Generally the amount of such metal component will be between about 0.1 and about 10 percent based on the weight of the porous tectosilicate. The Group VIII metal may be introduced from a suitable source, e.g., chloroplatinic acid, and impreganted on the porous zeolite either before or after the treatment of the zeolite resulting in the enhanced activity thereof. Alternatively, the Group VIII metal may be incorporated into the catalyst by ion exchange of a suitable Group VIII metal solution with the catalyst. Again, the acid activity of the catalyst may be enhanced either before or after the ion exchange procedure. The Group VIII metal component may also be deposited on a separate support, generally an inorganic oxide such as alumina, which supported metal is thereafter combined in particle form with the porous zeolite of enhanced acid activity. All of these methods of incorporating a Group VIII metal component into the catalyst are those conventionally used in the art and the details thereof will be apparent to those skilled in the art. It is contemplated that any Group VIII metal may be employed, i.e., iron, cobalt, nickel or metal of the platinum series. Particularly preferred are platinum and palladium.

The isomerization process described herein may operate at pressure from about atmospheric to superatmospheric. Generally, it is contemplated that the pressure utilized in the present process will be between about 0 and about 1000 psig, and preferably between about 100 and 500 psig.

Temperature of the process will vary with the nature of the paraffinic charge stock. Generally, the temperature employed is within the approximate range of 200 to 900 degrees F.

The amount of hydrogen present to produce formation of branched chain isomers in accordance with the process of this invention is governed by the nature of the paraffinic hydrocarbons reacted as well as the nature of the reaction per se. In general, the molar ratio between hydrogen and the hydrocarbons may extend from about 0.1:1 to about 20:1.

The following examples will serve to illustrate the process of the invention without limiting the same.

EXAMPLE 1

An HZSM-5 catalyst having a silica/alumina ratio of 70 and an alpha activity ($\alpha$) of 270 was subjected to a two hour treatment at 1000 degrees F. using a mixture of gases made up of nitrogen flowing at 50 cc/minute after passage through a water evaporator maintained at 65 degrees C. and thereafter blended with an ammonia gas stream flowing at 15 cc/minute. The catalyst after such treatment had an enhanced alpha value ($\alpha$) of 885 and was then impregnated with a solution of chloroplatinic acid to a 0.6 weight percent platinum level.

The resulting catalyst was compared to another HZSM-5 catalyst having an alpha value of 162 impregnated in similar fashion to a 0.5 weight percent platinum level.

The two catalysts were evaluated for n-pentane isomerization at the following conditions: 200 psig, hydrogen to hydrocarbon ratio of 1, liquid hourly space velocity of 4 and a temperature of 450 degrees F. The results obtained are summarized below:

| Catalyst | Percent Conversion to Iso-pentane |
| --- | --- |
| Conventional HZSM-5; $\alpha$ = 162 | 4 |
| Enhanced HZSM-5; $\alpha$ = 885 | 12 |
| The selectivity to iso-pentane was | 99–100 percent. |

EXAMPLE 2

The catalysts of Example 1 were evaluated for n-pentane isomerization under the conditions of Example 1, except that a temperature of 500 degrees F. was employed.

The results obtained are shown below:

| Catalyst | Percent Conversion to Iso-pentane |
| --- | --- |
| Conventional HZSM-5; $\alpha$ = 162 | 22 |
| Enhanced HZSM-5; $\alpha$ = 885 | 49 |
| The selectivity to iso-pentane was | 99–100 percent |

EXAMPLE 3

The enhanced catalyst of Example 1, having an alpha value of 885 and containing 0.6 weight percent platinum was evaluated for n-hexane isomerization. At a pressure of one atmosphere, $H_2$/HC ratio of 10, LHSV of 6.9 and a temperature of 500 degrees F., the conversion of n-hexane to its isomers was 80.5 percent with the selectivity to the isomers being about 99 percent.

EXAMPLE 4

An HZSM-12 catalyst having a silica/alumina ratio of 90 with an intrinsic alpha activity ($\alpha$) of 110 was treated to give a catalyst having an enhanced alpha value of 334. The enhanced catalyst was impregnated with a solution of chloroplatinic acid to a 0.4 weight percent platinum level.

The resulting catalyst was evaluated for n-hexane isomerization under reaction conditions including a pressure of one atmosphere, $H_2$/HC ratio of 10, LHSV of 0.22 and a temperature of 500 degrees F. The conversion to hexane isomers was 98.4 percent with selectivities to the isomers being 98 percent.

It will be seen from the above experimental results that improved yields of iso-paraffin product are obtained utilizing the specified crystalline zeolite catalysts which have undergone pretreatment to enhance the alpha activity thereof to a value of greater than about 300.

It will be apparent to those skilled in the art that the above examples can be successfully repeated with ingredients and under conditions equivalent to those set forth above.

From the foregoing specification, one skilled in the art can readily ascertain the essential features of this invention and without departing from the spirit and scope thereof can adapt it to various alternative applications.

We claim:

1. A process for effecting hydroisomerization of a $C_4$–$C_8$ paraffin which comprises contacting a feedstock containing the paraffin under hydroisomerization conditions with a catalyst comprising a porous crystalline zeolite characterized by silica/alumina mole ratio of greater than 12 and a constraint index within the approximate range of 1 to 12, which zeolite contains a minor proportion of a Group VIII metal and which zeolite has an enhanced acid activity achieved by a method comprising treating the zeolite with water under conditions of contact time, temperature and water partial pressure governed by the following relationship of treating time and water pressure at constant temperature:

$$0.01(Pt)_T < (Pt) < 10(Pt)_T$$

where
 $(Pt)_T = 2.6 \times 10^{-9} e^{16000/T}$;
 P = Water Partial Pressure, atmospheres;
 t = Treating Time, hours;
 T = Temperature, degrees K.

2. The process of claim 1 wherein the acid activity of said catalyst is enhanced by subjecting said catalyst to controlled pretreatment with water for a sufficient time to produce the zeolite having the acid activity, expressed as alpha, of at least about 300.

3. The process of claim 1 wherein said paraffin is a normal paraffin.

4. The process of claim 1 wherein said paraffin is a cycloparaffin.

5. The process of claim 3 wherein said paraffin is n-hexane, n-pentane or mixtures thereof.

6. The process of claim 4 wherein said paraffin is cyclohexane.

7. The process of claim 1 wherein said porous crystalline zeolite is ZSM-5.

8. The process of claim 1 wherein said porous crystalline zeolite is ZSM-11.

9. The process of claim 1 wherein said porous crystalline zeolite is ZSM-12.

10. The process of claim 1 wherein said porous crystalline zeolite is ZSM-23.

11. The process of claim 1 wherein said porous crystalline zeolite is ZSM-35.

12. The process of claim 1 wherein said porous crystalline zeolite is ZSM-38.

13. The process of claim 1 wherein said hydroisomerization conditions include a temperature between about 200 and about 900 degrees F., a pressure between about 0 and about 1000 psig, a liquid hourly space velocity between about 0.1 and about 50 and a hydrogen to hydrocarbon mole ratio between about 0.1:1 and about 20:1.

14. The process of claim 2 wherein said controlled pretreatment involves contact with liquid water.

15. The process of claim 2 wherein said controlled pretreatment involves contact with steam.

16. The process of claim 2 wherein ammonia is added to the water in an amount of from between about 0.01 to about 10 mole ratio of ammonia to water.

17. The process of claim 16 wherein said porous zeolite has a crystal size of 0.01 to 0.05 microns and said relationship of treating time and water pressure at constant temperature is as follows:

$$0.01(Pt)_T < (Pt) < 1.0(Pt)_T.$$

18. The process of claim 2 wherein said acid activity is between about 300 and about 10,000.

19. The process of claim 1 wherein said minor proportion of a Group VIII metal is between about 0.01 and about 10 weight percent.

20. The process of claim 1 wherein said Group VIII metal is platinum.

21. The process of claim 1 wherein said Group VIII metal is palladium.

22. The process of claim 17 wherein ammonia is added to the water in an amount of about 0.1 to about 1.0 mole ratio of ammonia to water.

23. The process of claim 13 wherein the hydroisomerizaton conditions include a pressure of between about 100 and about 500 psig.

* * * * *

UNITED STATES PATENT AND TRADEMARK OFFICE
CERTIFICATE OF CORRECTION

PATENT NO. : 4,374,296
DATED : February 15, 1983
INVENTOR(S) : WERNER O. HAAG and RUDOLPH M. LAGO It is certified that error appears in the above—identified patent and that said Letters Patent is hereby corrected as shown below:

On The Title Page,

Abstract, line 5, "silica/aluminum" should be --silica/alumina--.

Column 1, line 49, "weigtt" should be --weight--.

Signed and Sealed this

Fifth Day of July 1983

[SEAL]

Attest:

GERALD J. MOSSINGHOFF

Attesting Officer  Commissioner of Patents and Trademarks